US 6,804,458 B2

(12) United States Patent
Sherwood et al.

(10) Patent No.: US 6,804,458 B2
(45) Date of Patent: Oct. 12, 2004

(54) AEROSOL GENERATOR HAVING HEATER ARRANGED TO VAPORIZE FLUID IN FLUID PASSAGE BETWEEN BONDED LAYERS OF LAMINATE

(75) Inventors: Timothy S. Sherwood, Midlothian, VA (US); Scott A. Sowers, Richmond, VA (US); Sirisha P. Reddy, Atlanta, GA (US); F. Murphy Sprinkel, Jr., Glen Allen, VA (US); Kenneth A. Cox, Midlothian, VA (US); Walter A. Nichols, Chesterfield, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 15 days.

(21) Appl. No.: 10/003,852

(22) Filed: Dec. 6, 2001

(65) Prior Publication Data

US 2003/0108342 A1 Jun. 12, 2003

(51) Int. Cl.$^7$ ............................ F22B 35/06; F22B 37/12
(52) U.S. Cl. ..................... 392/397; 392/391; 122/242
(58) Field of Search .................................. 392/386, 390, 392/394, 395, 396, 397, 398; 122/235.11, 242, 243; 261/99, 104, 109; 239/128, 135, 136; 128/203.12, 203.16, 203.17, 203.26, 203.24; 131/273, 194

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paulins et al. |
| 3,162,324 A | 12/1964 | Houser |
| 3,431,393 A | 4/1969 | Katsuda |
| 3,486,663 A | 12/1969 | Humphrey |
| 3,658,059 A | 4/1972 | Steil |

(List continued on next page.)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | 953409 | 6/1994 |
| WO | 94/09842 A | 5/1994 |
| WO | 98/17131 | 4/1998 |

OTHER PUBLICATIONS

Written Opinion for PCT/US02/38685 dated Sep. 15, 2003.
Barry, P.W. et al. "In Vitro Comparison of the Amount of Salbuzamol Available for Inhalation From Different Formulations Used with Different Spacer Devices" Eur Respir J 1997; 10: 1345–1348.
Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

(List continued on next page.)

*Primary Examiner*—Sang Y. Paik
(74) *Attorney, Agent, or Firm*—Burns, Doane, Swecker & Mathis, LLP

(57) ABSTRACT

An aerosol generator includes a fluid supply which supplies fluid to a fluid passage and a heater which heats the fluid into a gaseous state, the fluid passage being located between opposed layers of a laminate. The fluid passage can be a capillary sized passage formed by locating a mandrel between opposed layers of the laminate, bonding the layers together and removing the mandrel such that the space previously occupied by the mandrel forms the fluid passage. The opposed layers of the laminate can be copper sheets and ceramic layers can be provided on the outside of the copper layers. The aerosol generator can be used to generate aerosols containing medicated materials.

4 Claims, 4 Drawing Sheets

U.S. PATENT DOCUMENTS

| | | | |
|---|---|---|---|
| 3,716,416 A | 2/1973 | Adihart et al. | |
| 3,750,961 A | 8/1973 | Franz | |
| 3,847,304 A | 11/1974 | Cohen | |
| 3,859,398 A | 1/1975 | Havstad | |
| 3,902,635 A | 9/1975 | Jinotti | |
| 3,903,883 A | 9/1975 | Pecina et al. | |
| 3,904,083 A | 9/1975 | Little | |
| 3,967,001 A | 6/1976 | Almaula et al. | |
| 3,987,941 A | 10/1976 | Blessing | |
| 3,993,246 A | 11/1976 | Erb et al. | |
| 4,042,153 A | 8/1977 | Callahan et al. | |
| 4,060,082 A | 11/1977 | Lindberg et al. | |
| 4,077,542 A | 3/1978 | Petterson | |
| 4,161,282 A | 7/1979 | Erb et al. | |
| 4,162,501 A | 7/1979 | Mitchell et al. | |
| 4,212,347 A * | 7/1980 | Eastman | 165/46 |
| 4,215,708 A | 8/1980 | Bron | |
| 4,231,492 A | 11/1980 | Rios | |
| 4,258,073 A | 3/1981 | Payne | |
| 4,261,356 A | 4/1981 | Turner et al. | |
| 4,289,003 A | 9/1981 | Yang | |
| 4,291,838 A | 9/1981 | Williams | |
| 4,303,083 A | 12/1981 | Burruss, Jr. | |
| 4,383,171 A | 5/1983 | Sinha et al. | |
| 4,391,308 A | 7/1983 | Steiner | |
| 4,395,303 A | 7/1983 | Weir | |
| 4,433,797 A | 2/1984 | Galia | |
| 4,471,892 A | 9/1984 | Coleman | |
| 4,512,341 A | 4/1985 | Lester | |
| 4,575,609 A | 3/1986 | Fassel et al. | |
| 4,627,432 A | 12/1986 | Newell et al. | |
| 4,649,911 A | 3/1987 | Knight et al. | |
| 4,682,010 A | 7/1987 | Drapeau et al. | |
| 4,695,625 A | 9/1987 | Macdonald | |
| 4,700,657 A | 10/1987 | Butland | |
| 4,730,111 A | 3/1988 | Vestal et al. | |
| 4,735,217 A | 4/1988 | Gerth et al. | |
| 4,744,932 A | 5/1988 | Browne | |
| 4,749,778 A | 6/1988 | Fukuzawa et al. | |
| 4,762,995 A | 8/1988 | Browner et al. | |
| 4,776,515 A | 10/1988 | Michalchik | |
| 4,790,305 A | 12/1988 | Zoltan et al. | |
| 4,811,731 A | 3/1989 | Newell et al. | |
| 4,819,625 A | 4/1989 | Howe | |
| 4,819,834 A | 4/1989 | Thiel | |
| 4,829,996 A | 5/1989 | Noakes et al. | |
| 4,837,260 A | 6/1989 | Sato et al. | |
| 4,848,374 A | 7/1989 | Chard et al. | |
| 4,871,115 A | 10/1989 | Hessey | |
| 4,871,623 A | 10/1989 | Hoopman et al. | |
| 4,877,989 A | 10/1989 | Drews et al. | |
| 4,911,157 A | 3/1990 | Miller | |
| 4,922,901 A | 5/1990 | Brooks et al. | |
| 4,926,852 A | 5/1990 | Zoltan et al. | |
| 4,935,624 A | 6/1990 | Henion et al. | |
| 4,941,483 A | 7/1990 | Ridings et al. | |
| 4,947,875 A | 8/1990 | Brooks et al. | |
| 4,974,754 A | 12/1990 | Wirz | |
| 4,982,097 A | 1/1991 | Slivon et al. | |
| 4,992,206 A | 2/1991 | Waldrop | |
| 5,021,802 A | 6/1991 | Allred | |
| 5,044,565 A | 9/1991 | Alexander | |
| 5,056,511 A | 10/1991 | Ronge | |
| 5,060,671 A | 10/1991 | Counts et al. | |
| 5,063,921 A | 11/1991 | Howe | |
| 5,096,092 A | 3/1992 | Devine | |
| 5,125,441 A | 6/1992 | Mette | |
| 5,133,343 A | 7/1992 | Johnson, IV et al. | |
| 5,134,993 A | 8/1992 | van der Linden et al. | |
| 5,135,009 A | 8/1992 | Muller et al. | |
| 5,144,962 A | 9/1992 | Counts et al. | |
| 5,151,827 A | 9/1992 | Ven et al. | |
| 5,178,305 A | 1/1993 | Keller | |
| 5,184,776 A | 2/1993 | Minier | |
| 5,217,004 A | 6/1993 | Blasnik et al. | |
| 5,226,441 A | 7/1993 | Dunmire et al. | |
| 5,228,444 A | 7/1993 | Burch | |
| 5,230,445 A | 7/1993 | Rusnak | |
| 5,231,983 A | 8/1993 | Matson et al. | |
| 5,259,370 A | 11/1993 | Howe | |
| 5,290,540 A | 3/1994 | Prince et al. | |
| 5,298,744 A | 3/1994 | Mimura et al. | |
| 5,299,565 A | 4/1994 | Brown | |
| 5,322,057 A | 6/1994 | Raabe et al. | |
| 5,327,915 A | 7/1994 | Porenski et al. | |
| 5,342,180 A | 8/1994 | Daoud | |
| 5,342,645 A | 8/1994 | Eisele et al. | |
| 5,349,946 A | 9/1994 | McComb | |
| 5,395,445 A | 3/1995 | Bohanan | |
| 5,421,489 A | 6/1995 | Holzner, Sr. et al. | |
| 5,462,597 A | 10/1995 | Jubran | |
| 5,474,059 A | 12/1995 | Cooper | |
| 5,565,677 A | 1/1996 | Wexler | |
| 5,515,842 A | 5/1996 | Ramseyer et al. | |
| 5,516,383 A * | 5/1996 | Jha et al. | 148/531 |
| 5,522,385 A | 6/1996 | Lloyd et al. | |
| 5,556,964 A | 9/1996 | Hofstraat et al. | |
| 5,564,442 A | 10/1996 | MacDonald et al. | |
| 5,575,929 A | 11/1996 | Yu et al. | |
| 5,585,045 A | 12/1996 | Heinonen et al. | |
| 5,617,844 A | 4/1997 | King | |
| 5,642,728 A | 7/1997 | Andersson et al. | |
| 5,674,860 A | 10/1997 | Carling et al. | |
| 5,682,874 A | 11/1997 | Grabenkort et al. | |
| 5,730,158 A | 3/1998 | Collins et al. | |
| 5,743,251 A | 4/1998 | Howell et al. | |
| 5,756,995 A | 5/1998 | Maswadeh et al. | |
| 5,765,724 A | 6/1998 | Amberg et al. | |
| 5,823,178 A | 10/1998 | Lloyd et al. | |
| 5,839,430 A | 11/1998 | Cama | |
| 5,855,202 A | 1/1999 | Andrade | |
| 5,856,671 A | 1/1999 | Henion et al. | |
| 5,863,652 A | 1/1999 | Matsumura et al. | |
| 5,869,133 A | 2/1999 | Anthony et al. | |
| 5,872,010 A | 2/1999 | Karger et al. | |
| 5,878,752 A | 3/1999 | Adams et al. | |
| 5,881,714 A | 3/1999 | Yokoi et al. | |
| 5,906,202 A | 5/1999 | Schuster et al. | |
| 5,908,527 A * | 6/1999 | Abrams | 156/277 |
| 5,914,122 A | 6/1999 | Otterbeck et al. | |
| 5,932,249 A | 8/1999 | Gruber et al. | |
| 5,932,315 A | 8/1999 | Lum et al. | |
| 5,934,272 A | 8/1999 | Lloyd et al. | |
| 5,934,273 A | 8/1999 | Andersson et al. | |
| 5,944,025 A | 8/1999 | Cook et al. | |
| 5,954,979 A | 9/1999 | Counts et al. | |
| 5,957,124 A | 9/1999 | Lloyd et al. | |
| 5,970,973 A | 10/1999 | Gonda et al. | |
| 5,970,974 A | 10/1999 | Van Der Linden et al. | |
| 5,978,548 A | 11/1999 | Holmstrand et al. | |
| 5,993,633 A | 11/1999 | Smith et al. | |
| 6,014,970 A | 1/2000 | Ivri et al. | |
| 6,053,176 A | 4/2000 | Adams et al. | |
| 6,054,032 A | 4/2000 | Haddad et al. | |
| 6,069,214 A | 5/2000 | McCormick et al. | |
| 6,069,219 A | 5/2000 | McCormick et al. | |
| 6,070,575 A | 6/2000 | Gonda et al. | |
| 6,071,428 A | 6/2000 | Franks et al. | |
| 6,076,522 A | 6/2000 | Dwivedi et al. | |
| 6,077,543 A | 6/2000 | Gordon et al. | |
| 6,080,721 A | 6/2000 | Patton | |

| | | |
|---|---|---|
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Ganan-Calvo |
| 6,116,893 A | 9/2000 | Peach |
| 6,119,953 A | 9/2000 | Ganan-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Ganán-Calvo |
| 6,182,712 B1 | 2/2001 | Stout et al. |
| 6,187,214 B1 | 2/2001 | Ganán-Calvo |
| 6,187,344 B1 | 2/2001 | Eljamal et al. |
| 6,189,803 B1 | 2/2001 | Ganán-Calvo |
| 6,192,882 B1 | 2/2001 | Gonda |
| 6,196,219 B1 | 3/2001 | Hess et al. |
| 6,197,835 B1 | 3/2001 | Ganán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Ganán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,586,110 B1 * | 7/2003 | Obeshaw .................... 428/593 |
| 2001/0032647 A1 | 10/2001 | Schuster et al. |

OTHER PUBLICATIONS

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology". Respiratory Drug Delivery VI (eds Dalby, R.N., Byron, P.R. & Farr, S.J.) Interpharm Press, Buffalo Grove, IL 1998 pp. 97–102.

Hou, Shugang et al. *Solution Stability of Budensonide in Novel Aerosol Formulations* Abstract No. 2582, Solid State Physical Pharmacy, Nov. 17, 1998, p. S–307.

Kousaica, Yasuo et al., "Generation of Aerosol Particles by Boiling of Suspensions", Aerosol Science and Technology, 21:236–240 (1994) (023).

Moren, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers. Impurities, and Content of the Glucocorticold Budesonide and Preparation of Primary Standard, Journal of Pharmaceutical Sciences, vol. 69, No. 7, pp. 766–770, Jul. 1980.

Notification of Transmittal of International Preliminary Examination Report dated Mar. 30, 204 for PCT/US02/38685.

* cited by examiner

FIG. 1

- MOUTHPIECE 18
- OUTLET 26
- HEATER 24
- PASSAGE 16
- SENSOR 20
- CONTROLLER 22
- VALVE 14
- FLUID RESERVOIR 12
- AEROSOL GENERATOR 10

FIG. 2

- HEATER 36
- AEROSOL GENERATOR 30
- PASSAGE 34
- FLUID RESERVOIR 32

US 6,804,458 B2

AEROSOL GENERATOR HAVING HEATER ARRANGED TO VAPORIZE FLUID IN FLUID PASSAGE BETWEEN BONDED LAYERS OF LAMINATE

BACKGROUND OF THE INVENTION

1. Field of the Invention

The present invention relates generally to aerosol generators and, more particularly, to vapor driven aerosol generators. The aerosol generators of the invention are able to generate aerosols without requiring the use of compressed gas propellants. The present invention also relates to methods for generating an aerosol. The present invention has particular applicability to the generation of aerosols containing medicated material.

2. Description of the Related Art

Aerosols are gaseous suspensions of fine solid or liquid particles and are useful in a wide variety of applications. For example, medicated liquids and powders may be administered in aerosol form. Such medicated aerosols include, for example, materials which are useful in the treatment of respiratory ailments, in which case the aerosols may be inhaled into a patient's lungs. Aerosols may also be used in non-medicinal applications including, for example, dispensing air fresheners, applying perfumes and delivering paints and/or lubricants.

In aerosol inhalation applications, it is typically desirable to provide an aerosol having an average mass median particle diameter of less than 2 microns to facilitate deep lung penetration. Most known aerosol generators are incapable of generating aerosols having an average mass median particle diameter less than from 2 to 4 microns. Also, in certain applications, it is generally desirable to deliver medicated material at high flow rates, for example, above 1 mg per second. Most known aerosols suited for delivering medicated material are incapable of delivering material at such high flow rates while maintaining a suitable average mass median particle diameter. In addition, most known aerosol generators deliver an imprecise amount of aerosol compared with the amount of aerosol that is intended to be delivered.

The related art discloses aerosol generators which employ various techniques for delivering an aerosol. A particularly useful technique involves volatilizing a fluid and ejecting the volatilized fluid into the atmosphere. The volatilized fluid subsequently condenses, thereby forming an aerosol. See, for example, commonly assigned U.S. Pat. No. 5,743,251, the entire contents of which document are hereby incorporated by reference. Such aerosol generators may eliminate or conspicuously reduce some or all of the aforementioned problems associated with the known aerosol generators. However, since these aerosol generators employ heat-generating systems, heat resistive material and, in some cases, various control devices, pumps and valves, the manufacture and assembly of such aerosol generators can be complicated and expensive.

In light of the foregoing, there exists a need in the art for the provision of an aerosol generator which overcomes or conspicuously ameliorates the above described shortcomings in the related art. Accordingly, it is an object of the present invention to provide a vapor driven aerosol generator which produces an aerosol from a fluid by volatilizing the fluid and directing the volatilized fluid therefrom.

Other objects and aspects of the present invention will become apparent to one of ordinary skill in the art upon review of the specification, drawings and claims appended hereto.

SUMMARY OF THE INVENTION

The invention provides an aerosol generator which includes a fluid passage located between opposed layers of a laminate. The layers can comprise copper sheets and the fluid passage can comprise a space formed by locating a mandrel between the copper sheets, bonding the layers together and removing the mandrel. A heater can be arranged to heat fluid in the passage into a gaseous state such that the vaporized fluid ejected from the fluid passage condenses in ambient air and forms an aerosol.

The laminate can include ceramic layers sandwiching the copper layers and the ceramic layers can be bonded to the copper layers at the time the copper layers are bonded together. The heater can comprise a layer of resistance heating material located on one or more of the ceramic layers so as to conduct heat into the fluid passage.

BRIEF DESCRIPTION OF THE DRAWINGS

The objects and advantages of the invention will become apparent from the following detailed description of the preferred embodiments thereof in connection with the accompanying drawings, in which:

FIG. 1 is a schematic diagram of an exemplary aerosol generator in accordance with the invention;

FIG. 2 is a top cut-away view of an embodiment of the aerosol generator;

DETAILED DESCRIPTION OF THE PREFERRED EMBODIMENTS OF THE INVENTION

Figure 3A:
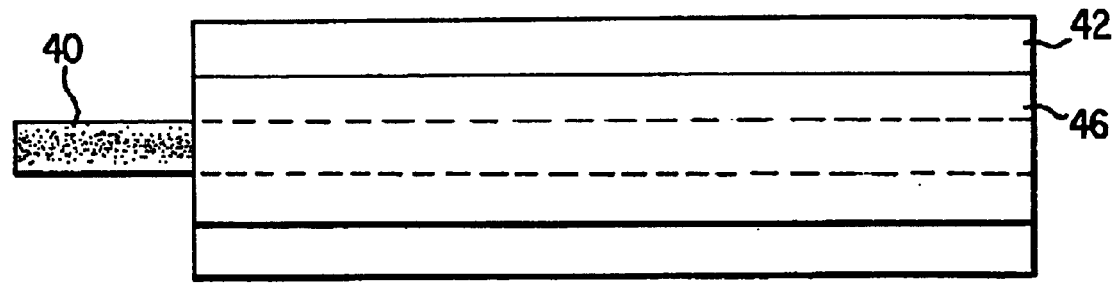
FIGS. 3 A–C show details of how a portion of the aerosol generator shown in FIG. 1 can be assembled.

When referring to the drawing figures, like reference numerals designate identical or corresponding elements throughout the several figures.

FIG. 1 shows a vapor driven aerosol generator 10 in accordance with one embodiment of the invention. As shown, the aerosol generator 10 includes a source 12 of fluid, a valve 14, a passage 16, a mouthpiece 18, an optional sensor 20 and a controller 22. In addition, the aerosol generator 10 includes a heater 24. The controller 22 includes suitable electrical connections and ancillary equipment such as a battery which cooperates with the controller for operating the valve 14, the sensor 20 and the heater 24. In operation, the valve 14 can be opened to allow a desired volume of fluid from the source 12 to enter the passage 16 prior to or subsequent to detection by the sensor 20 of vacuum pressure applied to the mouthpiece 18 by a user attempting to inhale aerosol from the inhaler 10. As fluid is supplied to the passage 16, the controller 22 operates the heater 24 to drive the fluid out of the passage 16, i.e., the controller 22 operates the heater 24 to heat the fluid to a suitable temperature for volatilizing the fluid therein. The volatilized fluid exits an outlet 26 of the passage 16 and the volatilized fluid forms an aerosol which can be inhaled by a user drawing upon the mouthpiece 18.

The aerosol generator shown in FIG. 1 can be modified to utilize different fluid supply arrangements. For instance, the fluid source can comprise a delivery valve which delivers a predetermined volume of fluid to the passage 16 and/or the passage 16 can include a chamber of predetermined size to accommodate a predetermined volume of fluid to be volatilized during an inhalation cycle. In the case where the passage includes a chamber to accommodate a volume of fluid, the device can include a valve downstream of the chamber for preventing flow of the fluid beyond the chamber during filling thereof. If desired, the chamber can include a preheater arranged to heat fluid in the chamber such that a vapor bubble expands and drives the remaining liquid from the chamber into the passage 16. Details of such a preheater arrangement can be found in commonly owned U.S. patent application Ser. No. 09/742,395 filed on Dec. 22, 2000, the disclosure of which is hereby incorporated by reference. If desired, the valve(s) could be omitted and the fluid source 12 can include a delivery arrangement such as a syringe pump which supplies a predetermined volume of fluid to the chamber or directly to the passage 16. The heater 24 can be an individual heater or a plurality of heaters arranged to volatilize the liquid in passage 16. In the case of manual operations, the sensor 20 can be omitted such as in the case where the aerosol generator 10 is operated manually by a mechanical switch, electrical switch or other suitable technique.

FIG. 2 shows a top cut-away view of an aerosol generator 30 in accordance with an embodiment of the invention wherein the aerosol generator 30 includes a fluid supply 32, a passage 34, and a heater 36. The heater 36 can be arranged inside the passage 34 or located on an outer surface of a layer of material in which the passage is located. If desired, a plurality of heaters can be arranged to heat the fluid in the passage, e.g., heaters located on opposite sides of the passage or a series of heaters located along the length of the passage. The heater or heaters are preferably thin films of resistance heating material. In order to pass electrical current through the heaters, the heaters can be in electrical contact with suitable electrical contacts and a suitable power source such as a battery can be used to deliver sufficient direct current to the contacts in order to heat the heater or heaters to desired temperatures. However, other types of heaters can be used such as an induction heating arrangement as disclosed in commonly owned U.S. patent application Ser. No. 09/742,323 filed Dec. 22, 2000, the disclosure of which is hereby incorporated by reference. Operation of the heaters and supply of fluid from the fluid source can be controlled by a suitable controller as in the case of the first embodiment.

The embodiments shown in FIGS. 1 and 2 can be made from a laminate construction wherein the passage can comprise a channel in a first layer and a second layer overlying the first layer encloses the channel. In one embodiment of the invention, a mandrel is used to form the passage. For example, a mandrel having a predetermined outer diameter is arranged in a stack of layers of the laminate and after the layers are bonded together, the mandrel is removed to provide the fluid passage with a desired size. For example, the mandrel can comprise a wire such as a stainless steel wire having a diameter of 0.01 to 10 mm, preferably 0.05 to 1 mm, and more preferably 0.1 to 0.5 mm and a preferred length of 50 to 200 times the width to provide a flow passage of capillary size and the mandrel can be located between metal layers such as two copper sheets. Alternatively, the capillary passage can be defined by transverse cross sectional area of the passage which can be $8 \times 10^{-5}$ to 80 mm$^2$, preferably $2 \times 10^{-3}$ to $8 \times 10^{-1}$ mm$^2$ and more preferably $8 \times 10^{-3}$ to $2 \times 10^{-1}$ mm$^2$.

In order to provide a heater for generating aerosol in the aerosol generator, the copper/wire laminate could be located between ceramic layers and one or more layers of resistance heating material such as a thin film of platinum can be selectively located at desired locations on the ceramic layers, e.g., a thin film resistor can be deposited in a thickness and/or pattern which provides a desired value of resistance, suitable electrical connections, and/or a desired heating rate. The layers of the laminate can be adhesively or metallurgically bonded together. For example, the laminate can be metallurgically bonded together by heating the laminate to a temperature effective to wet and bond the copper layers together without causing the copper sheets to bond to the stainless steel wire. After the laminate is bonded together, the wire can be removed from the bonded laminate to form a fluid passage between the copper sheets.

Figure 3B:
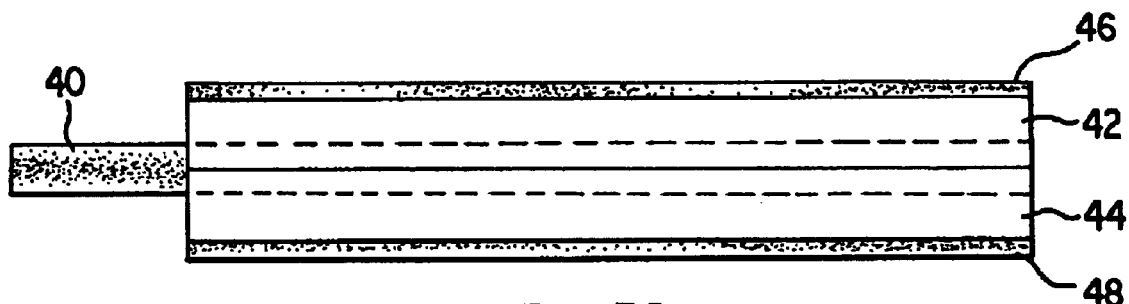
Figure 3C:
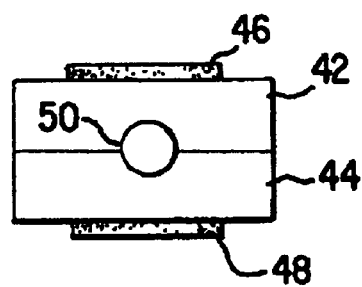
Figure 4A:
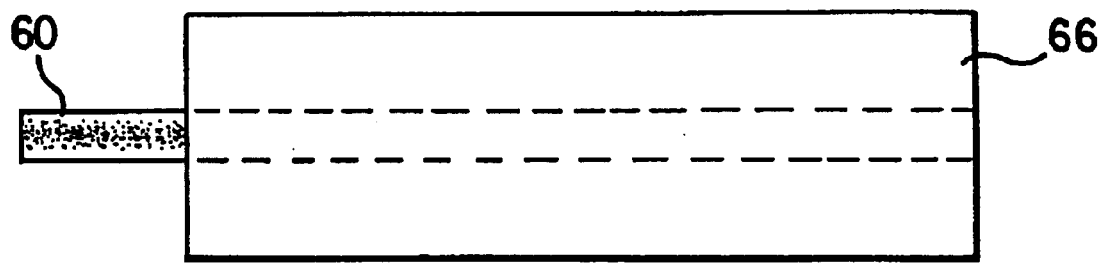
FIGS. 4 A–F show details of how a laminated heater for the aerosol generator of FIG. 1 can be assembled.
Figure 4B:
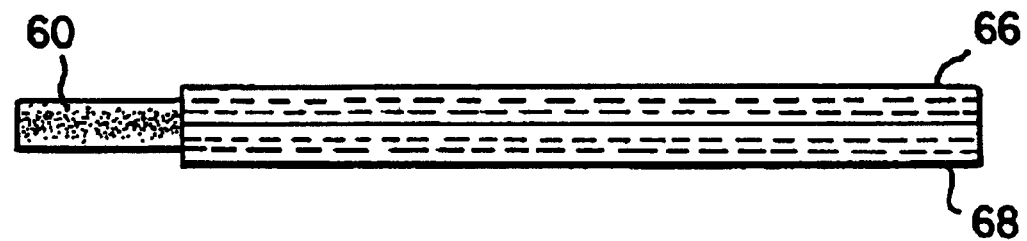
Figure 4C:
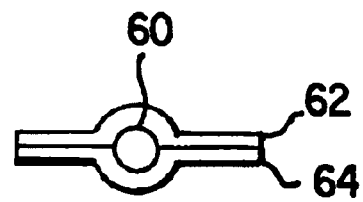
Figure 4D:
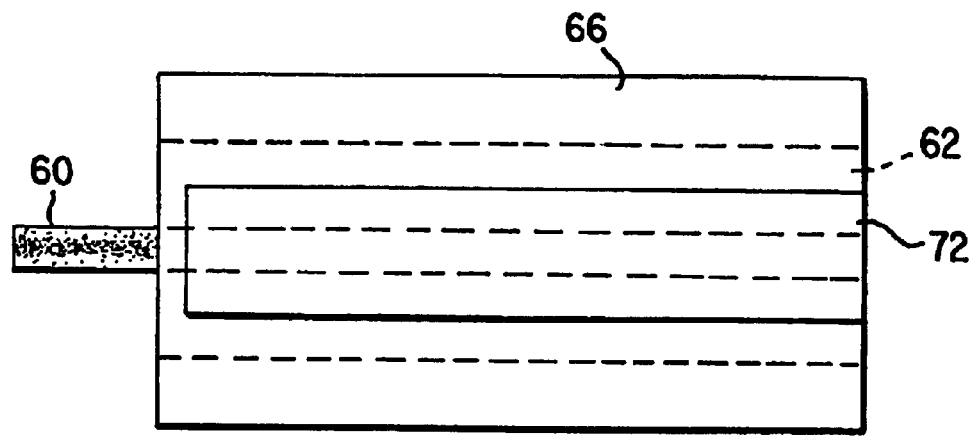
Figure 4E:
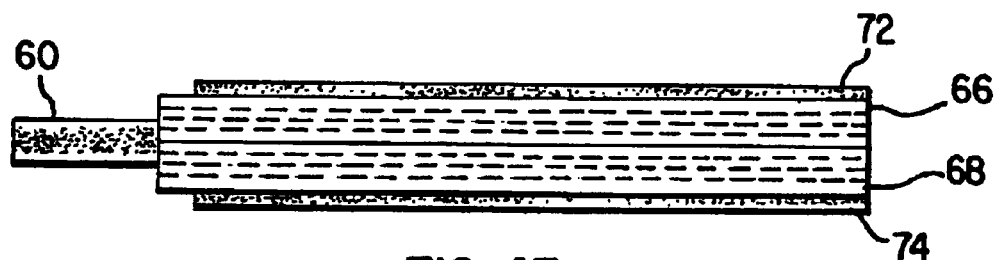
Figure 4F:
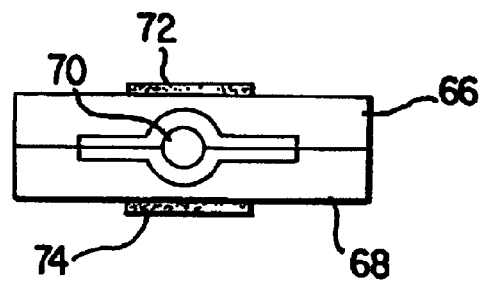

FIGS. 3 A–C show details of a first embodiment of a heater arrangement made using a mandrel as described above. As shown in FIGS. 3 A–B, a mandrel 40 is located between layers 42, 44 of ceramic green tape which are placed above and below the mandrel 40. The ceramic green tapes are then compressed to conform to the shape of the mandrel and the laminated structure is fired in an oven such as a tube furnace to sinter the ceramic material and bond the layers 42, 44 together. The mandrel is then removed from the laminated structure leaving a fluid passage 50 extending through the laminate. In order to provide a heating element or elements, a suitable resistance heating material such as platinum can be located on the outer surfaces of the laminate. For example, a pair of platinum heaters 46, 48 can be sputtered on the outer surfaces of layers 42, 44, as shown in FIG. 3C. The heaters 46, 48 can be coextensive with the outer surfaces of the layers 42, 44 or have other dimensions such as those shown in FIGS. 3 A–C wherein the heaters extend the length of the passage 50 but have widths which are smaller than the width of the layers 42, 44.

FIGS. 4 A–F show details of another heater arrangement wherein a mandrel 60 is placed between metal layers. In this example, copper sheets or foils 62, 64 having any suitable thickness such as 0.001–0.005 inch are cut to desired dimensions and a suitably sized mandrel 60 such as a 32 gauge stainless steel tube is placed between the copper layers. The sheets are compressed to conform to the shape of the mandrel 60. The copper laminate is placed between ceramic green tapes 66, 68 which are deformed under pressure to conform to the shape of the copper laminate having the mandrel therein, as shown in FIG. 4C. The laminated structure is fired in an oven such as a tube furnace to sinter the ceramic material and bond the layers 62, 64, 66, 68 together. The mandrel is then removed from the laminated structure leaving a fluid passage 70 extending through the laminate. In order to provide a heating element or elements, a suitable resistance heating material such as platinum can be located on the outer surfaces of the laminate. For example, a pair of platinum heaters 72, 74 can be sputtered on the outer surfaces of layers 66, 68, as shown in FIGS. 4 D–F. The heaters 72, 74 can be coextensive with the outer surfaces of the layers 66, 68 or have other dimensions such as those shown in FIGS. 4 D–F wherein the heaters extend substantially along the length of the passage 70 but have widths which are smaller than the width of the layers 66, 68.

While two embodiments of a heater arrangement are described above, the heater arrangement can be made by other techniques. For example, while ceramic and metal layers are described in the foregoing embodiments, if desired, the laminate can include organic material such as a polymer material. However, the heater arrangement can also be made from a single layer of material which has been machined, etched or otherwise modified to form the passage. Alternatively, one or more additional layers can be interposed between the layers so as to form the passage. The heater or heaters can be arranged to extend vertically along an inner sidewall of the passage. In arrangements wherein the heater contacts the fluid, it is desirable to form the heater of an inert material such as platinum or coat the heater with a material which is non-reactive with the fluid, e.g., glass or metal such as stainless steel.

In a further exemplary embodiment of the invention, a capillary in a ceramic laminate is fabricated by laser machining a channel in a ceramic material such as alumina. The channel in the laser machined ceramic substrate can be enclosed by a ceramic layer bonded to the ceramic substrate by a bonding material such as an adhesive or metallurgical bond. For example, the ceramic layer can be bonded to the ceramic substrate by epoxy or a copper eutectic bond. Eutectic bonded copper is preferred since it offers greater control over the areas to be bonded. In order to provide one or more heating elements for heating fluid in the passage, one or more layers of resistance heating material such as a thin film of platinum can be selectively located at desired locations on the ceramic layers. For purposes of metallurgically bonding the ceramic layers together, one or more copper layers can be provided between the ceramic layers and the ceramic laminate can be heated to a temperature such as above 1050° C. to wet and bond the copper to the ceramic layers. At the ceramic/copper interface, the copper would eutectic bond to the ceramic layers.

As an example of a technique for manufacturing a multi-layer laminate which includes a fluid passage and a heater for volatilizing fluid delivered to the fluid passage, a 290 $\mu$m width channel can be laser machined in an aluminum oxide layer having length and width dimensions of 10 mm by 10 mm by 0.125 or 0.250 mm thick and a similarly sized aluminum oxide layer can enclose the top of the channel and form a fluid passage of desired size in the ceramic laminate. The aluminum oxide layers can be sealed by a conventional epoxy metallized glass or the like. In order to provide a fluid path between the fluid passage and a fluid supply, a 32 gauge needle (0.004 inch inner diameter and 0.009 inch outer diameter) can be adhesively bonded to the ceramic laminate. The thin film resistor can comprise a platinum layer having dimensions of 0.29 mm×10 mm×0.005 mm at 0.69 $\Omega$ deposited on the backside of the ceramic laminate. The thin film resistor can be deposited in a pattern which provides a desired value of resistance, suitable electrical connections, and/or a desired heating rate. In order to generate an aerosol, liquid in the passage is heated by the resistor such that the liquid ejected from the passage as a vapor expands and condenses into an aerosol.

The fluid may include any material capable of volatilization by the aerosol generator. In a preferred embodiment, the fluid does not decompose when exposed to the heat required for volatilization thereof. The fluid preferably includes a medicated material such as, for example, a material that is useful in the treatment of respiratory ailments. In such applications, the generated aerosol may be inhaled into a user's lungs. Alternatively, the fluid may comprise a non-medicated material such as an aroma generating fluid.

In the foregoing embodiments, the fluid passage can be defined by a capillary tube or a channel in a multi-layered arrangement wherein the layers are formed from a heat-resistant material that is preferably capable of withstanding the temperatures and pressures generated in the fluid passage. The heat-resistant material is more preferably capable of withstanding repeated heating cycles. Also, the heat-resistant material preferably does not react with the fluid contained in the fluid passage. The heat-resistant material may include, for example, alumina, zirconia, silica, aluminum silicate, titania, yttria-stabilized zirconia, glass or mixtures thereof, preferably alumina. The layers may be of any size suitable for aerosol generation. According to a preferred embodiment, each layer can have a length of from about 1 to 100 mm, more preferably about 15 mm; a width of from about 1 to 100 mm, more preferably about 15 mm; and a thickness of from about 0.001 to 10 mm, more preferably about 0.25 mm.

The layers can be configured to at least partially define the fluid passage. In an exemplary embodiment of the present invention, a channel is in a layer or the channel can be defined by adding one or more layers of material between first and second layers. The layers can be attached together, thereby enclosing the channel therebetween. In this manner, the channel defines the fluid passage.

The layers may be attached together using various techniques, including, for example, adhesive bonding. The adhesive material used to attach the layers is preferably capable of withstanding repeated heating cycles and may include, for example, a metal, a cement, an epoxy, an acrylic, a cyanoacrylic or mixtures thereof, preferably an acrylic cement. Alternatively, other techniques may be used to attach the layers together such as, for example, mechanical or metallurgical bonding such as a brazing material, metallized glass or the like.

The fluid passage is preferably linear to facilitate the flow of the fluid therethrough. Alternatively, the fluid passage can be non-linear in two or three dimensions such as in the case where the direction of fluid flow through the passage contains at least one turn. An outlet at the downstream end of the fluid passage can be sized to achieve a desired aerosol particle size distribution. In a preferred embodiment, the outlet is circular and has a diameter of about from 0.01 to 5 mm, more preferably about 0.2 mm.

The outlet may be disposed at an angle, for example, 10 to 160°, with respect to the axis of fluid flow within the fluid passage, to direct the flow of the volatilized fluid out of the fluid passage in a desired direction. According to an alternative embodiment, the fluid passage can extend through a side wall of the layers, and the outlet can be defined by the furthest downstream portion of the fluid passage. A conduit (not shown) may be connected to receive the volatilized fluid from the outlet to further direct the flow of volatilized fluid in a desired direction.

Such a conduit can have a diameter of from about 0.01 to 5 mm.

In a preferred embodiment, a valve and/or a pump can be used to control the flow of fluid from the fluid supply to the fluid passage. The valve and/or the pump may be manually operated or a controller may manipulate the valve and/or the pump based on various parameters including, for example, the amount of time the valve remains in the open position, or the volumetric amount of fluid that is supplied to the fluid passage. In this manner, the valve and/or the pump may enable the liquid supply to deliver a predetermined volume of fluid in liquid phase to the fluid passage. In an alternative embodiment, the fluid in liquid phase can be contained in a chamber, and the fluid can be delivered by compressing the fluid in the chamber using a piston.

The fluid supply provides the fluid to be volatilized in liquid phase to the fluid passage. The fluid in liquid phase may be stored in the liquid supply at a pressure above atmospheric to facilitate delivery of the fluid to the fluid passage. In an exemplary embodiment, the fluid supply comprises a refillable storage chamber formed of a material suitable for containing the fluid to be volatilized. Alternatively, the fluid supply comprises a disposable storage chamber which, upon exhaustion of the fluid, is discarded and replaced by a new storage chamber.

The fluid passage may contain any amount of fluid in liquid phase which is capable of being volatilized by the heater of the aerosol generator. For example, the fluid passage may have a liquid volumetric capacity of from about $1 \times 10^{-6}$ ml to 0.005 ml. Alternatively, the fluid passage may have a liquid volumetric capacity of greater than about 0.005 ml, preferably from about 0.1 ml to 1.0 ml. In aerosol inhalation applications, the fluid passage may have a liquid volumetric capacity which is sufficient for containing a predetermined amount of fluid that comprises a metered quantity of fluid.

The heater for heating the fluid passage preferably includes a film forming an electrically resistive heating material which is different from the heat-resistant material used to form the layers of the aerosol generator. For example, the resistive material may include a pure metal, metal alloy or metal compound such as platinum, titanium nitride, stainless steel, nickel chromium or mixtures thereof. Additional resistive materials include composite layers such as self-regulating heater materials. The main heater may be sized to be capable of generating a sufficient amount of heat to vaporize the fluid present in the fluid passage. In a preferred embodiment, the heater has a length of from about 1 to 100 mm, e.g., more preferably about 10 mm; a width of from about 0.1 to 10 mm, e.g., more preferably about 0.5 mm; a thickness of from about 1 to 10 microns, e.g., more preferably about 3 microns; and an electrical resistance of from about 0.1 to 10 ohms, e.g., more preferably about 0.65 ohm.

Using a material for forming the heater which is different from the material used to form the layers allows the resistance through the heater to be easily adjusted by varying various parameters including, for example, the dimensions and the material of the heater. In this manner, the resistance of the heater and the amount of heat produced by the heater may be adjusted for various applications.

The resistive material of the heater may be attached to the layers using various techniques. For example, the resistive material may be sputtered, printed, bonded or coated upon the layers. Deposition by sputtering includes, for example, DC magnetron sputter deposition. Deposition by bonding includes, for example, eutectically bonding the resistive material using sputtered material including, for example, copper or copper sheet material. Alternatively, vacuum evaporation, chemical deposition, electroplating and chemical vapor deposition may be used to deposit the resistive material.

Various factors contribute to the stability of the bond between the heater and the layers. For example, to enhance bonding, the arithmetic average of the surface roughness of the surface upon which the resistive material is disposed preferably is greater than or equal to about 1 microinch, more preferably from about 1 to 100 microinches, and most preferably from about 12 to 22 microinches. In addition, the heat-resistant material of the layers and the resistive material of the heater preferably have comparable coefficients of thermal expansion to minimize or prevent thermally induced delamination.

In a preferred embodiment, the heater is in electrical contact with first and second contacts which pass an electrical current through the heater. In this embodiment, the power supply which provides the electrical current to the heater is in electrical contact with the first and second contacts.

The first and second contacts of the heater are preferably formed from a material which has a lower resistance than that of the resistive material of the heater. For example, the first and second contacts typically include copper or a copper alloy such as, for example, phosphor bronze and Si bronze, and preferably copper or a copper alloy comprising at least 80% copper. Use of such materials prevents or reduces the heating of the contacts prior to the heating of the heater. The contacts are sized to be capable of passing an electrical current through the heater. The contacts may be attached to the layers and/or heater using any of the techniques used to attach the resistive material to the layers, as discussed above.

In each of the above embodiments, a single heater or multiple heaters may be used for heating the fluid in the passage. The use of multiple heaters may enable a more uniform distribution of heat within the fluid passage. Alternatively, the use of multiple heaters may enable different zones of the fluid passage to be maintained at different temperatures. Such differing temperature zones in the fluid passage may be useful in fluid temperature control devices, as discussed in U.S. patent application Ser. No. 09/742,322 filed on Dec. 22, 2000, the entire contents of which document are incorporated by reference herein.

The aerosol generator may generate an aerosol either on an intermittent or continuous basis. For intermittent generation of an aerosol, for example, the liquid supply provides the fluid in liquid phase to the fluid passage each time the generation of an aerosol is desired. The valve and/or the pump may be used to actuate the flow of fluid from the liquid supply to the fluid passage. The remaining fluid in liquid phase between the liquid supply and the fluid passage can be prevented from traveling back into the liquid supply by any suitable device such as a valve and/or the pump to prevent expansion of the volatilized fluid in the direction opposite the outlet.

For generating an intermittent aerosol in inhalation applications, the aerosol generator is preferably provided with a puff-actuated sensor, which is preferably arranged inside a mouthpiece disposed proximate to the outlet. The puff-actuated sensor can be used to actuate the valve and/or the pump and the heater so that the liquid supply provides the fluid in liquid phase to the fluid passage and the fluid is volatilized by the heater. The puff-actuated sensor is preferably sensitive to pressure drops occurring in the mouthpiece when a user draws on the mouthpiece. The aerosol generator is preferably provided with circuitry such that, when a user draws on the mouthpiece, the valve and/or pump supply fluid in liquid phase to the fluid passage and the heater is heated by the power supply.

A puff-actuated sensor suitable for use in the aerosol generator includes, for example, Model 163PC01D35 silicon sensor, manufactured by the MicroSwitch division of Honeywell, Inc., located in Freeport, Ill., or SLP004D 0-4" $H_2O$ Basic Sensor Element, manufactured by SenSym, Inc., located in Milpitas, Calif. Other known flow-sensing devices, such as those using hot-wire anemometry principles, may also be suitable for use with the aerosol generator.

While the invention has been described in detail with reference to preferred embodiments thereof, it will be apparent to one skilled in the art that various changes can be made, and equivalents employed, without departing from the scope of the invention.

What is claimed is:

1. An aerosol generator, comprising:

a laminate body having a fluid passage therein, the fluid passage being located between opposed layers of the laminate body which are bonded together, the laminate body including metal and ceramic layers, inner surfaces of the metal layers being bonded together at first and second locations separated by the fluid passage, the ceramic layers being bonded to outer surfaces of the metal layers, and the fluid passage being a capillary sized passage having a maximum width of 0.01 to 10 mm; a heater arranged to heat liquid in the fluid passage into a gaseous state; and a fluid supply arranged to provide a fluid to the fluid passage.

2. The aerosol generator of claim 1, wherein the metal layers comprise copper sheets.

3. The aerosol generator of claim 1, wherein the heater is located on at least one of the ceramic layers.

4. The aerosol generator of claim 1, wherein the ceramic layers comprise layers of a material selected from the group consisting of alumina, zirconia, silica and mixtures thereof.

* * * * *